United States Patent
Krongauz et al.

(10) Patent No.: US 6,891,038 B2
(45) Date of Patent: May 10, 2005

(54) PHOTOCHROMIC SPIRO(INDOLINE) NAPHTHOXAZINES

(75) Inventors: Valeri Krongauz, Rehovot (IL); Alexandre Chif, Rostov-on-Don (RU); Alexander Aizikovich, Ramat Gan (IL); Vladimir Tchernoivanov, Rostov-on-Don (RU)

(73) Assignee: Yeda Research and Development Co. Ltd., Rehovot (IL)

( * ) Notice: Subject to any disclaimer, the term of this patent is extended or adjusted under 35 U.S.C. 154(b) by 43 days.

(21) Appl. No.: 10/239,306
(22) PCT Filed: Apr. 5, 2001
(86) PCT No.: PCT/IL01/00317
§ 371 (c)(1), (2), (4) Date: Sep. 20, 2002
(87) PCT Pub. No.: WO01/77112
PCT Pub. Date: Oct. 18, 2001

(65) Prior Publication Data
US 2003/0114669 A1 Jun. 19, 2003

(30) Foreign Application Priority Data
Jul. 6, 2000 (IL) ................................. 137207
Apr. 6, 2002 (IL) ................................. 135531

(51) Int. Cl.[7] .......................................... C07D 498/10
(52) U.S. Cl. ......................................... 544/71; 252/586
(58) Field of Search ............................................. 544/71

(56) References Cited

U.S. PATENT DOCUMENTS

| | | | |
|---|---|---|---|
| 4,851,530 A | 7/1989 | Rickwood | |
| 4,913,544 A | 4/1990 | Rickwood et al. | |
| 4,959,471 A | 9/1990 | Melzig | |
| 5,186,867 A | 2/1993 | Castaldi et al. | |
| 5,405,958 A | 4/1995 | VanGemert | |
| 5,446,149 A | 8/1995 | Rickwood et al. | |
| 5,446,150 A | 8/1995 | Rickwood et al. | |
| 5,446,151 A | 8/1995 | Rickwood et al. | |
| 5,473,068 A | 12/1995 | Krongauz et al. | |
| 5,833,885 A | 11/1998 | Rickwood et al. | |
| 5,936,016 A | 8/1999 | Lareginie et al. | |
| 6,004,486 A | 12/1999 | Chan | |
| 6,030,555 A | 2/2000 | Chan | |

FOREIGN PATENT DOCUMENTS

| WO | WO 99/01457 | 1/1999 |
|---|---|---|
| WO | 99 20630 | 4/1999 |

OTHER PUBLICATIONS

Patent Abstract of Japan, *Photochromic Material*, Suga Atsuo, application No. 02075535, application date Mar. 27, 1990; publication No. 03275789, publication date 03275789.

Crano et al., "Spiroxazines and their use in photochromic lenses", *Applied Photochromic Polymer Systems*, (C.B. McArdle, Ed) Blackie & Sons, Glasgow, London, (1992), pp. 31–76.

*Primary Examiner*—Mark L Berch
*Assistant Examiner*—Kahsay Habte
(74) *Attorney, Agent, or Firm*—Browdy and Neimark, P.L.L.C.

(57) ABSTRACT

A photochromic compound for incorporation into plastic articles, particularly into a plastic lens, is selected from a spiro(indoline)naphtho(2,1-b)(1,4)oxazine and a spiro(indoline)naphtho(1,2-b)(1,4)oxazine containing a group selected from: (a) —$CH_2$—$C_nF_{2n+1}$ at the nitrogen atom in the 1-position on the indoline part of the molecule, wherein n is an integer of 1 to 6; (b) —COOR at the 3-position on the indoline part of the molecule, wherein R is (i) C1–C6 alkyl optionally substituted by fluoro, C1–C4 alkoxy or fluoroalkoxy, C1–C4 alkylcarbonyloxy, C2–C4 alkenylcarbonyloxy, C3–C6 cycloalkyl or aryl; (ii) C2–C6 alkenyl with a terminal double bond; (iii) C3–C6 cycloalkyl optionally substituted by fluoro; or (iv) aryl; (c) an —$OCF_3$ group on the benzene ring of the indoline part of the molecule; (d) an aryl(dialkyl)methyl group of the formula —C(aryl)($C_nH_{2n+1}$)($C_mH_{2m+1}$), wherein n and m are integers from 1 to 5, linked to one of the benzene rings of the naphthoxazine part of the molecule; and (e) any combination of (a), (b), (c) and/or (d).

7 Claims, No Drawings

PHOTOCHROMIC SPIRO(INDOLINE) NAPHTHOXAZINES

FIELD OF THE INVENTION

The present invention relates to certain novel photochromic spiro(indolino)naphthoxazine compounds and to articles comprising them.

BACKGROUND OF THE INVENTION

Spiro(indolino)oxazine compounds have been found to be useful for imparting photochromic properties to a polymeric host material. Examples of spirooxazine and their use in photochromic lenses have been reviewed by Crano et al. in Applied Photochromic Polymer Systems (C. B. McArdle, Ed.) Blackie & Sons, Glasgow, London, 1992, pp. 31–76. As a rule, the unsubstituted spiroindolinonaphthoxazines give a rather low optical density of the blue color on exposure to light.

Several U.S. patents describe spiro(indoline)naphtho(2,1-b)(1,4)oxazine compounds (see for example U.S. Pat. Nos. 4,959,471 (Melzig), 4,913,544, 5,446,149, 5,446,150, 5,446, 151 (Rickwood et al.), 5,186,867 (Castaldi et al.), 5,405,958 (Van Gemert), 5,936,016 (Lareginie et al.), 6,004,486 and 6,030,555 (You-Ping Chan)) that are said to give enhanced optical density on exposure to sunlight. The enhancement of the photoinduced optical density was achieved mainly by introducing electron-donor or -acceptor substituents in the naphthalene moiety of the molecule, while the absorption maximum of the colored form remains in the region of 570–630 nm.

U.S. Pat. Nos. 4,851,530 and 5,833,885 (Rickwood et al) describe spirooxazines showing substantial change in the kinetic and spectral properties of spirooxazines by modification of the 1-position in the indoline ring with the absorption maxima of the photoactivated form shorter than 570 nm (mainly red). PCT Publication No. WO 99/20630 describe photochromic spiro (indoline)naphtho( 1,2-b)(1,4)oxazine compounds.

The present invention relates to novel spiro(indoline) naphtho(2,1-b) (1,4)oxazine and spiro(indoline)naphtho(1, 2-b)(1,4)oxazine compounds that have particular substituents on the indoline and/or on the naphthalene part of the molecule. None of the publications mentioned above describe the compounds of the present invention.

SUMMARY OF THE INVENTION

The present invention relates to novel photochromic spiro (indoline)naphtho(2,1-b) (1,4)oxazine and spiro(indoline) naphtho(1,2-b) (1,4)oxazine compounds containing certain particular groups as follows:

(a) —$CH_2$—$C_nF_{2n+1}$ at the nitrogen atom in the 1-position on the indoline part of the molecule, wherein n is an integer of 1 to 6;

(b) —COOR at the 3-position on the indoline part of the molecule, wherein R is (i) $C_1$–$C_6$ alkyl optionally substituted by fluoro, $C_1$–$C_4$ alkoxy or fluoroalkoxy, $C_1$–$C_4$ alkylcarbonyloxy, $C_2$–$C_4$ alkenylcarbonyloxy, $C_3$–$C_6$ cycloalkyl or aryl; (ii) $C_2$–$C_6$ alkenyl with a terminal double bond; (iii) $C_3$–$C_6$ cycloalkyl optionally substituted by fluoro; or (iv) aryl;

(c) an —$OCF_3$ group on the benzene ring of the indoline part of the molecule;

(d) an aryl(dialkyl)methyl group of the formula —C(aryl) ($C_nH_{2n+1}$)($C_mH_{2m+1}$), wherein n and m are integers from 1 to 5, linked to one of the benzene rings of the naphthoxazine part of the molecule; and (e) any combination of (a), (b), (c) and/or (d).

The photochromic compounds of the present invention provide a substantial increase of the photoactivation and decoloration rates while retaining a high optical density in the photoactivated state. Incorporation of these compounds into a plastic lens or another plastic article provides the articles with desirable photochromic properties.

DETAILED DESCRIPTION OF THE INVENTION

In one preferred embodiment of the present invention, the spiro(indoline)naphtho(2,1-b)(1,4)oxazine and spiro (indoline)naphtho(1,2-b)(1,4) oxazine compounds have at the nitrogen atom in the 1-position on the indoline part of the molecule a radical —$CH_2$—$C_nF_{2n+1}$, and have the formulas Ia and Ib, respectively:

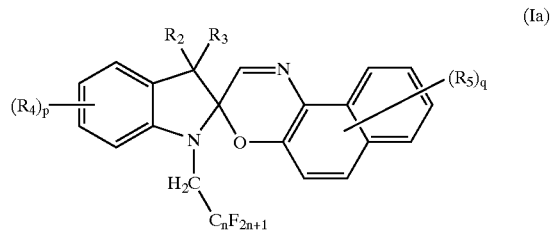

(Ia)

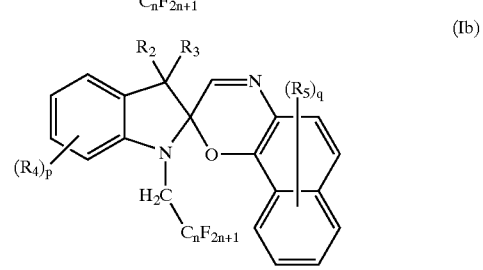

(Ib)

wherein (a) n is an integer from 1 to 6; p is 1 or 2; and q is an integer from 1 to 6;

(b) $R_2$ and $R_3$ represent independently a radical selected from: (i) $C_1$–$C_6$ alkyl optionally substituted by fluoro, $C_1$–$C_4$ alkoxy or fluoroalkoxy, $C_1$–$C_4$ alkylcarbonyloxy, $C_2$–$C_4$ alkenylcarbonyloxy, $C_3$–$C_6$ cycloalkyl or aryl-; (ii) $C_2$–$C_6$ alkenyl with a terminal double bond; (iii) $C_3$–$C_6$ cycloalkyl optionally substituted by fluoro; (iv) aryl; (v) alkylcarbonyl; or (vi) one of $R_2$ and $R_3$ is a group —COOR wherein R is a radical (i) to (iv) as defined hereinbefore and the other of $R_2$ and $R_3$ is a radical (i) to (iv) as defined hereinbefore; or (vii) $R_2$ and $R_3$ together with the carbon atom at position 3 of the indoline ring form a 3–7 membered saturated ring optionally containing a heteroatom selected from nitrogen, oxygen or sulfur, and (c) $R_4$ and $R_5$ represent independently (i) hydrogen; (ii) halogen, preferably fluoro; or a radical selected from: (iii) cyano; (iv) aryloxy optionally substituted by $C_1$–$C_6$ alkyl, $C_1$–$C_4$ alkoxy or amino; (v) $C_1$–$C_4$ alkoxy optionally substituted by halogen, preferably di- and trifluoromethoxy; (vii) $C_1$–$C_6$ alkyl optionally substituted by $C_1$–$C_4$ alkoxy, halogen, preferably trifluoromethyl, $C_3$–$C_6$ cycloalkyl, polycycloalkyl (such as norbomane or adamantane), aryl or heterocyclyl; (viii) aryl optionally substituted with amino or alkoxy group, preferably dialkylaminophenyl or methoxyphenyl; (ix) amide (—$CONH_2$); (x) sulfonamide (—$SO_2NH_2$); (xi) —$NR_6R_7$, wherein $R_6$ and $R_7$ are independently selected from alkyl, alkenyl, cycloalkyl, aryl, alkylaryl, fluoroalkyl (preferably trifluoromethyl) or $R_6$ and $R_7$ together with the nitrogen atom form a 3–7 membered saturated ring optionally containing a further heteroatom selected from nitrogen, oxygen or sulfur atom, preferably piperidino, piperazino or morpholino; (xii) $R_4$ may further be —$OCF_3$, in which case p is 1; and (xiii) $R_5$ may further be an aryl(dialkyl)methyl group of the formula —C(aryl)$(C_nH_{2n+1})(C_mH_{2m+1})$, wherein n and m are integers from 1 to 5, linked to one of the benzene rings of the naphthoxazine part of the molecule, in which case q is an integer from 1 to 5.

In another preferred embodiment of the present invention, the spiro(indoline)naphtho(2,1-b)(1,4)oxazine and spiro(indoline)naphtho(1,2-b)(1,4) oxazine compounds have at the 3-position on the indoline part of the molecule a group —COOR, wherein R is selected from: (i) $C_1$–$C_6$ alkyl optionally substituted by fluoro, $C_1$–$C_4$ alkoxy or fluoroalkoxy, $C_1$–$C_4$ alkylcarbonyloxy, $C_2$–$C_4$ alkenylcarbonyloxy, $C_3$–$C_6$ cycloalkyl or aryl; (ii) $C_2$–$C_6$ alkenyl with a terminal double bond; (iii) $C_3$–$C_6$ cycloalkyl optionally substituted by fluoro; or (iv) aryl; and have the formulas IIa and IIb, respectively:

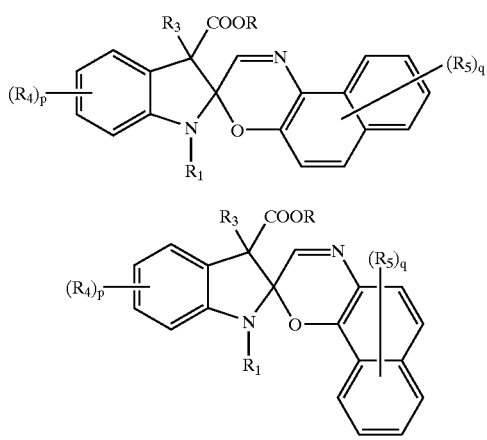

(IIa)

(IIb)

wherein
(a) p is 1 or 2 and q is an integer from 1 to 6;
(b) $R_1$ is a radical selected from: (i) $C_1$–$C_6$ alkyl optionally substituted by $C_1$–$C_4$ alkoxy, $C_1$–$C_4$ alkylcarbonyloxy, $C_2$–$C_4$ alkenylcarbonyloxy, $C_3$–$C_6$ cycloalkyl, polycycloalkyl, aryl or heterocyclic ring; (ii) $C_3$–$C_6$ cycloalkyl; (iii) polycycloalkyl: (iv) aryl; (v) heterocyclic ring; (vi) —$CH_2$—$C_nF_{2n+1}$ wherein n is an integer of 1 to 6; or (vii) $C_2$–$C_6$ alkenyl with a terminal double bond;
(c) $R_3$ represents a radical selected from: (i) $C_1$–$C_6$ alkyl optionally substituted by fluoro, $C_1$–$C_4$ alkoxy or fluoroalkoxy, $C_1$–$C_4$ alkylcarbonyloxy, $C_2$–$C_4$ alkenylcarbonyloxy, $C_3$–$C_6$ cycloalkyl or aryl; (ii) $C_2$–$C_6$ alkenyl with a terminal double bond; (iii) $C_3$–$C_6$ cycloalkyl optionally substituted by fluoro ; or (iv) aryl; and
(d) $R_4$ and $R_5$ represent independently (i) hydrogen; (ii) halogen, preferably fluoro; or a radical selected from: (iii) cyano; (iv) aryloxy optionally substituted by $C_1$–$C_6$ alkyl, $C_1$–$C_4$ alkoxy or amino; (v) $C_1$–$C_4$ alkoxy optionally substituted by halogen, preferably di- and trifluoromethoxy; (vii) $C_1$–$C_6$ alkyl optionally substituted by $C_1$–$C_4$ alkoxy, halogen, preferably trifluoromethyl, $C_3$–$C_6$ cycloalkyl, polycycloalkyl (such as norbomane or adamantane), aryl or heterocyclyl; (viii) aryl optionally substituted with amino or alkoxy group, preferably dialkylaminophenyl or methoxyphenyl; (ix) amide (—$CONH_2$); (x) sulfonamide (—$SO_2NH_2$); (xi) —$NR_6R_7$, wherein $R_6$ and $R_7$ are independently selected from alkyl, alkenyl, cycloalkyl, aryl, alkylaryl, fluoroalkyl (preferably trifluoromethyl) or $R_6$ and $R_7$ together with the nitrogen atom form a 3–7 membered saturated ring optionally containing a further heteroatom selected from nitrogen, oxygen or sulfur atom, preferably piperidino, piperazino or morpholino; (xii) $R_4$ may further be —$OCF_3$, in which case p is 1; and (xiii) $R_5$ may further be an aryl(dialkyl)methyl group of the formula —C(aryl)$(C_nH_{2n+1})(C_mH_{2m+1})$, wherein n and m are integers from 1 to 5, linked to one of the benzene rings of the naphthoxazine part of the molecule, in which case q is an integer from 1 to 5.

In a further preferred embodiment of the present invention, the spiro(indoline)naphtho(2,1-b)(1,4)oxazine and spiro(indoline)naphtho(1,2-b)(1,4) oxazine compounds have a trifluoromethoxy (—$OCF_3$) group on the benzene ring of the indoline part of the molecule, and have the formulas IIIa and IIIb, respectively:

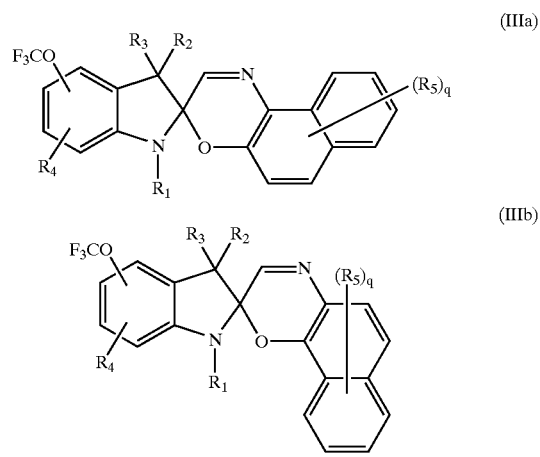

(IIIa)

(IIIb)

wherein
(a) q is an integer from 1 to 6;
(b) $R_1$ is a radical selected from: (i) $C_1$–$C_6$ alkyl optionally substituted by $C_1$–$C_4$ alkoxy, $C_1$–$C_4$ alkylcarbonyloxy. $C_2$–$C_4$ alkenylcarbonyloxy, $C_3$–$C_6$ cycloalkyl, polycycloalkyl, aryl or heterocyclic ring; (ii) $C_3$–$C_6$ cycloalkyl; (iii) polycycloalkyl: (iv) aryl; (v) heterocyclic ring; (vi) —$CH_2$-$C_nF_{2n+1}$ wherein n is an integer of 1 to 6; or (vii) $C_2$–$C_6$ alkenyl with a terminal double bond;
(c) $R_2$ and $R_3$ represent independently a radical selected from: (i) $C_1$–$C_6$ alkyl optionally substituted by fluoro, $C_1$–$C_4$ alkoxy or fluoroalkoxy, $C_1$–$C_4$ alkylcarbonyloxy, $C_2$–$C_4$ alkenylcarbonyloxy, $C_3$–$C_6$ cycloalkyl or aryl; (ii) $C_2$–$C_6$ alkenyl with a terminal double bond; (iii) $C_3$–$C_6$ cycloalkyl optionally substituted by fluoro; (iv) aryl; or (v) alkylcarbonyl; or (vi) one of $R_2$ and $R_3$ is a group —COOR wherein R is a radical (i) to (iv) as defined hereinbefore and the other of $R_2$ and $R_3$ is a radical (i) to (iv) as defined hereinbefore; or (vii) $R_2$ and $R_3$ together with the carbon atom at position 3 of the indoline ring form a 3–7 membered saturated ring optionally containing a heteroatom selected from nitrogen, oxygen or sulfur, and
(d) $R_4$ and $R_5$ represent independently (i) hydrogen; (ii) halogen, preferably fluoro; or a radical selected from: (iii) cyano; (iv) aryloxy optionally substituted by $C_1$–$C_6$ alkyl, $C_1$–$C_4$ alkoxy or amino; (v) $C_1$–$C_4$ alkoxy optionally substituted by halogen, preferably di- and trifluoromethoxy; (vii) $C_1$–$C_6$ alkyl optionally substituted by $C_1$–$C_4$ alkoxy, halogen, preferably trifluoromethyl, $C_3$–$C_6$ cycloalkyl, polycycloalkyl (such as norbornane or adamantane), aryl or heterocyclyl; (viii) aryl optionally substituted with amino or alkoxy group, preferably dialkylaminophenyl or methoxyphenyl; (ix) amide (—$CONH_2$); (x) sulfonamide (—$SO_2NH_2$); (xi) —$NR_6R_7$, wherein $R_6$ and $R_7$ are independently selected from alkyl, alkenyl, cycloalkyl, aryl, alkylaryl, fluoroalkyl (preferably trifluoromethyl) or $R_6$ and $R_7$ together with the nitrogen atom form a 3–7 membered saturated ring optionally containing a further heteroatom selected from nitrogen, oxygen or sulfur atom, preferably piperidino, piperazino or morpholino; and (xii) $R_5$ may further be an aryl(dialkyl)methyl group of the formula —C(aryl)($C_nH_{2n+1}$)($C_mH_{2m+1}$), wherein n and m are integers from 1 to 5, linked to one of the benzene rings of the naphthoxazine part of the molecule, in which case q is an integer from 1 to 5.

In still a further preferred embodiment of the present invention, the spiro(indoline)naphtho(2,1-b)(1,4)oxazine and spiro(indoline)naphtho(1,2-b)(1,4) oxazine compounds have an aryl(dialkyl)methyl group of the formula —C(aryl) ($C_nH_{2n+1}$)($C_mH_{2m+1}$), wherein n and m are integers from 1 to 5, linked to one of the benzene rings of the naphthoxazine part of the molecule, and have the formulas IVa and IVb, respectively:

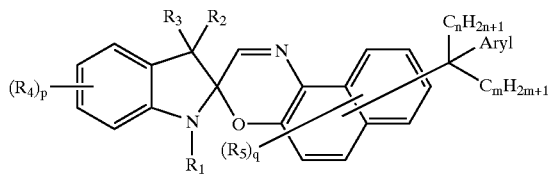

(IVa)

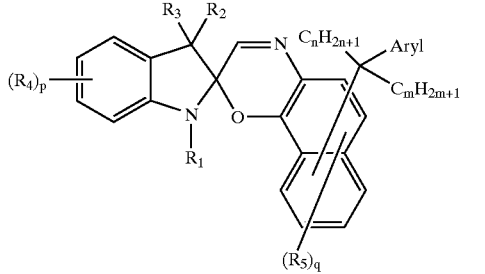

(IVb)

wherein
(a) p is 1 or 2 and q is an integer from 1 to 5;
(b) $R_1$ is a radical selected from: (i) $C_1$–$C_6$ alkyl optionally substituted by $C_1$–$C_4$ alkoxy, $C_1$–$C_4$ alkylcarbonyloxy, $C_2$–$C_4$ alkenylcarbonyloxy, $C_3$–$C_6$ cycloalkyl, polycycloalkyl, aryl or heterocyclic ring; (ii) $C_3$–$C_6$ cycloalkyl; (iii) polycycloalkyl: (iv) aryl; (v) heterocyclic ring; (vi) —$CH_2$—$C_nF_{2n+1}$ wherein n is an integer of 1 to 6; or (vii) $C_2$–$C_6$ alkenyl with a terminal double bond;
(c) $R_2$ and $R_3$ represent independently a radical selected from: (i) $C_1$–$C_6$ alkyl optionally substituted by fluoro, $C_1$–$C_4$ alkoxy or fluoroalkoxy, $C_1$–$C_4$ alkylcarbonyloxy, $C_2$–$C_4$ alkenylcarbonyloxy, $C_3$–$C_6$ cycloalkyl or aryl; (ii) $C_2$–$C_6$ alkenyl with a terminal double bond; (iii) $C_3$–$C_6$ cycloalkyl optionally substituted by fluoro; (iv) aryl; or (v) alkylcarbonyl; or (vi) one of $R_2$ and $R_3$ is a group —COOR wherein R is a radical (i) to (iv) as defined hereinbefore and the other of $R_2$ and $R_3$ is a radical (i) to (iv) as defined hereinbefore; or (vii) $R_2$ and $R_3$ together with the carbon atom at position 3 of the indoline ring form a 3–7 membered saturated ring optionally containing a heteroatom selected from nitrogen, oxygen or sulfur, and (d) $R_4$ and $R_5$ represent independently (i) hydrogen; (ii) halogen, preferably fluoro; or a radical selected from: (iii) cyano; (iv) aryloxy optionally substituted by $C_1$–$C_6$ alkyl, $C_1$–$C_4$ alkoxy or amino; (v) $C_1$–$C_4$ alkoxy optionally substituted by halogen, preferably di- and trifluoromethoxy; (vii) $C_1$–$C_6$ alkyl optionally substituted by $C_1$–$C_4$ alkoxy, halogen, preferably trifluoromethyl, $C_3$–$C_6$ cycloalkyl, polycycloalkyl (such as norbornane or adamantane), aryl or heterocyclyl; (viii) aryl optionally substituted with amino or alkoxy group, preferably dialkylaminophenyl or methoxyphenyl; (ix) amide (—$CONH_2$); (x) sulfonamide (—$SO_2NH_2$); (xi) —$NR_6R_7$, )wherein $R_6$ and $R_7$ are independently selected from alkyl, alkenyl, cycloalkyl, aryl, alkylaryl, fluoroalkyl (preferably trifluoromethyl) or $R_6$ and $R_7$ together with the nitrogen atom form a 3–7 membered saturated ring optionally containing a further heteroatom selected from nitrogen, oxygen or sulfur atom, preferably piperidino, piperazino or morpholino; and (xii) $R_4$ may further be —$OCF_3$, in which case p is 1.

According to the invention, the alkyl and alkoxy radicals may be linear or branched. The $C_2$–$C_4$ alkenylcarbonyloxy radical is preferably the radical derived from acrylic (—O—CO—CH=$CH_2$) or methacrylic (—O—CO—C($CH_3$)=$CH_2$) acid. The $C_3$–$C_6$ cycloalkyl is preferably cyclopentyl or cyclohexyl and the polycycloalkyl may be a $C_4$–$C_{20}$ bicycloalkyl such as partially or completely saturated naphthyl or a $C_6$–$C_{20}$ tricycloalkyl such as adamantyl and norbornyl. The $C_2$–$C_6$ alkenyl with a terminal double bond is preferably —$CH_2$—CH=$CH_2$ or —$CH_2$—($CH_2$)$_3$—CH=$CH_2$. The preferred radicals —$CH_2$—$C_nF_{2n+1}$ are —$CH_2$—$CF_3$ and —$CH_2$—$CF_2$—$CF_3$. fluoroalkoxy radical is preferably —$OCF_3$. When $R_5$ is an aryl(dialkyl)methyl group of the formula —C(aryl)($C_nH_{2n+1}$)($C_mH_{2m+1}$), n and m are preferably 1 such that said linking group is preferably tert-propylene ($CH_3$)—C—($CH_3$).

Further, the present invention provides synthetic methods for making the photochromic spirooxazine molecules of the invention. The compounds containing a COOR group on the 3-position of the indoline ring are prepared by the reaction of a Fischer base containing the aforementioned carboxylic ester structure at 3-position with the suitable 1-nitroso-2-naphthol non-substituted or substituted with one or more $R_5$ groups. The compounds containing a $F_3CO$— group on the benzene ring of the indoline molecule are prepared by the reaction of a Fischer base containing the aforementioned trifluoromethoxy group on the benzene ring with the suitable 1-nitroso-2-naphthol non-substituted or substituted with one or more $R_5$ groups. The compounds containing a —$CH_2$—$C_nF_{2n+1}$ group at the 1-position of the indoline ring are prepared by the reaction of a Fischer base containing the aforementioned polyfluoroalkyl group at the 1-position with the suitable 1-nitroso-2-naphthol non-substituted or substituted with one or more $R_5$ groups. The compounds wherein $R_5$ is an aryl(dialkyl)methyl group of the formula —C(aryl) ($C_nH_{2n+1}$)($C_mH_{2m+1}$), wherein n and m are integers from 1 to 5, linked to one of the benzene rings of the naphthoxazine part of the molecule, can be prepared by reaction between naphthol substituted with aryl(dialkyl)methyl group and the suitable Fisher base.

The photochromic compounds of the present invention and mixtures thereof and/or their mixtures with other photochromic compounds known in the art may be incorporated into a plastic lens, car window or other articles, giving high optical density of color on irradiation with sunlight. The aforementioned photochromic compounds or their mixtures can be incorporated into a plastic object, preferably a plastic lens, by any conventional method known in the art, for example, by molding techniques, e.g., injection molding, press-molding or by polymerization techniques, e.g., by thermal polymerization of a photochrome solution in a polymerizable monomer containing a catalyst, for example, azo-isobutyronytryl, giving free radicals on heating. Microencapsulation techniques can also be employed. A photochromic compound may be incorporated in a polymer host also by thermodiffusion through the lens surface. A mixture of different photochromes can be incorporated into a plastic object.

The present invention, thus, further relates to a photochromic article comprising a plastic object containing a photochromic compound of the present invention or mixtures thereof with a photochrome known in the art such as, but not being limited to, spirooxazines, naphthopyrans and fulgides. The article may also contain additives such as plasticizers, materials for the photochrome microencapsulation and light stabilizers such as hindered amines or phenols. The photochromic article is preferably a plastic lens.

The invention will now be illustrated by the following examples, to which it is not limited.

EXAMPLES

Example 1

Preparation of 1,3,3-Trimethyl-5-Trifluoromethoxy-Spiro-(Indoline-2,3'-(3H)-Naphtho[2,1-b]-(1,4)-Oxazine)

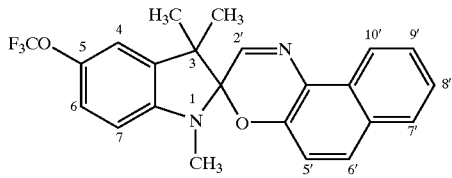

A solution of 1-nitroso-2-naphthol (0.50 g, 2.89 mmol) and 1,3,3-trimethyl-5-trifluoromethoxy-2-methyleneindoline (0.71 g, 2.77 mmol) in ethanol (30 ml) was heated under nitrogen and refluxed for 20 hrs. The solvent was then evaporated and the residue was chromatographed over silica (ethyl acetate/petroleum ether 1:10). After crystallization in ethanol, the yield of the pure product (colorless crystals) was 0.2 g (18%).

In the photoactivated colored form in the polystyrene film, the photochrome has a broad absorption band with maximum at 580 nm.

The compounds listed below as Examples 2–4 were prepared by a synthetic procedure analogous to that described in Example 1.

Example 2

1-Cyclohexylmethyl-3,3-Dimethyl-5-Trifluoromethoxy-6'-Dimethylamino-Spiro-(Indoline-2,3'-(3H)-Naphtho[2,1-b]-(1,4)-Oxazine)

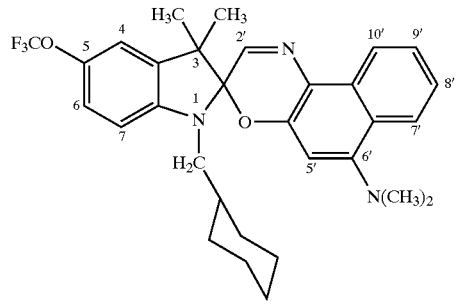

This compound presented an absorption band with $\lambda_{max}$ 555 nm in the photoactivated form.

Example 3

1-Propyl-3,3-Dimethyl-5-Trifluoromethoxy-6'-Dimethylamino-Spiro-(Indoline-2,3'-(3H)-Naphtho[2,1-b]-(1,4)-Oxazine)

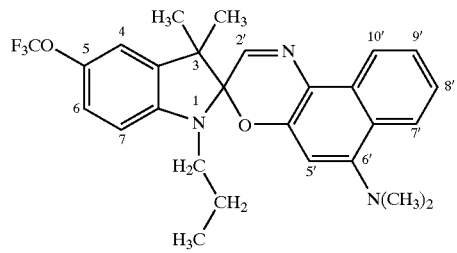

This compound presented an absorption band with $\lambda_{max}$ 550 nm in the photoactivated form.

Example 4

1-Propyl-3,3-Dimethyl-5-Trifluoromethoxy-6'-Piperidino-Spiro-(Indoline-2,3'-(3H)-Naphtho-[2,1-b]-(1,4)-Oxazine)

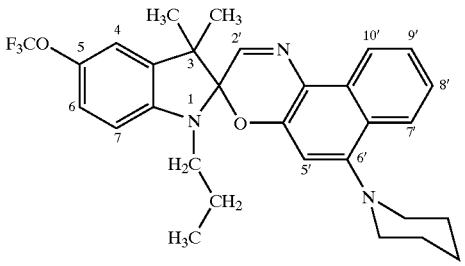

This compound presented an absorption band with $\lambda_{max}$ 558 nm in the photoactivated form.

Example 5 (Comparative)

The spirooxazines described in examples 1–4 and two known spirooxazines depicted by the formulas below were individually incorporated (5%) in a polystyrene film of 5 μm.

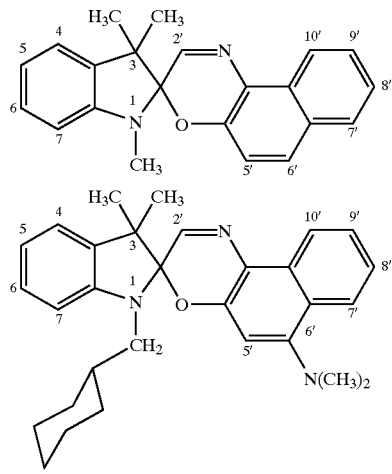

The results of the photochromic property examinations of the compounds are presented in Table 1, where OD is the optical density of the film at the photoinduced color absorption maximum ($\lambda_{max}$), $\tau_{1/2}$ is the halftime of color fading in the dark, and activation time is when the film reaches a steady-state color on irradiation with UV-light of a 250 W mercury lamp.

Table 1 shows that substitution in the phenyl ring of the indoline moiety with a trifluoromethoxy group brings about a profound hypsochromic shift, acceleration in the color decay and photoactivation processes.

Example 6

Preparation of 1,3-Dimethyl-3-Carboethoxy-Spiro-(Indoline-2,3'-(3H)-Naphtho[2,1-b]-(1,4)-Oxazine)

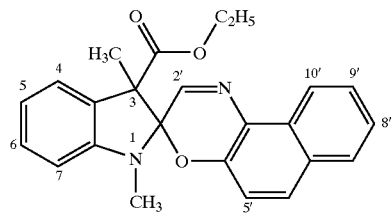

A solution of 1-nitroso-2-naphthol (0.50 g, 2.89 mmol) and 1,3-dimethyl-3-carboethoxy-2-methylene-indoline (0.87 g, 2.77 mmol) in ethanol (70 ml) was heated under nitrogen and refluxed for 2 hrs. The solvent was then evaporated and the residue was chromatographed over silica (ethyl acetate/petroleum ether 1:10). After crystallization in ethanol, the yield of the pure product (colorless crystals) was 0.21 g (16%).

In the photoactivated colored form in the polystyrene film, the photochrome has a broad absorption band with a maximum at 596 nm and a shoulder at 568 nm.

The compounds listed below as Examples 7–20 were prepared by a synthetic procedure analogous to that described in Example 6.

Example 7

1-Cyclohexylmethyl-3-Methyl-3-Carboethoxy-Spiro-(Indoline-2,3'-(3H)-Naphtho[2,1-b]-(1,4)-Oxazine)

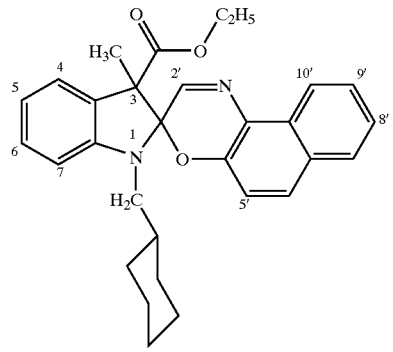

This compound presented a broad absorption band with $\lambda_{max}$ 602 nm and a shoulder at 568 nm in the photoactivated form.

Example 8

1,3,4,5-Tetramethyl-3-Carboethoxy-Spiro-(Indoline-2,3'-(3H)-Naphtho [2,1-b]-(1,4)-Oxazine).

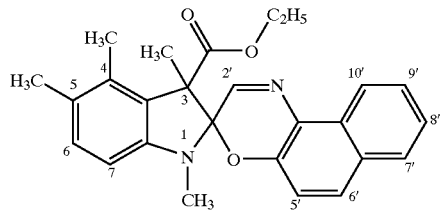

This compound presented a broad absorption band with $\lambda_{max}$ 612 nm and a shoulder at 574 nm in the photoactivated form.

Example 9

1,3,4,5-Tetramethyl-3-Carboethoxy-8'-(1-Methyl-1-Phenyl)Ethyl-Spiro-(Indoline-2,3'-(3H)-Naphtho[2,1-b]-(1,4)-Oxazine)

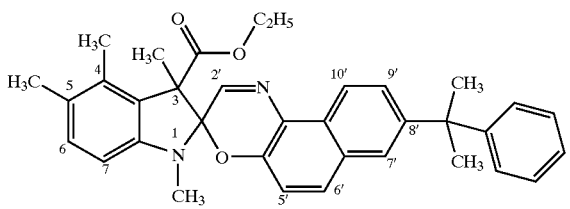

This compound presented a broad absorption band with $\lambda_{max}$ 580, 614 nm in the photoactivated form.

Example 10

1,3-Dimethyl-3-Carboethoxy-9'-Acetyloxy-Spiro-(Indoline-2,3'-(3H)-Naphtho-[2,1-b]-(1,4)-Oxazine).

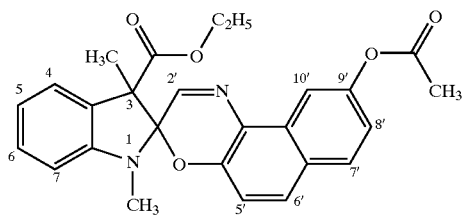

This compound presented a broad absorption band with $\lambda_{max}$ 575 593 nm in the photoactivated form.

Example 11

1-Isobutyl-3-Methyl-3-Carboethoxy-Spiro-(Indoline-2,3'-(3H)-Naphtho [2,1-b]-(1,4)-Oxazine).

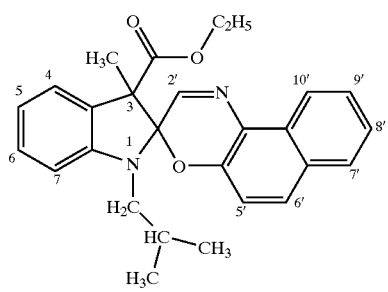

This compound presented a broad absorption band with $\lambda_{max}$ 570, 600 nm in the photoactivated form.

Example 12

1-Isobutyl-3,5-Dimethyl-3-Carboethoxy-Spiro-(Indoline-2,3'-(3H)-Naphtho[2,1-b]-(1,4)-Oxazine).

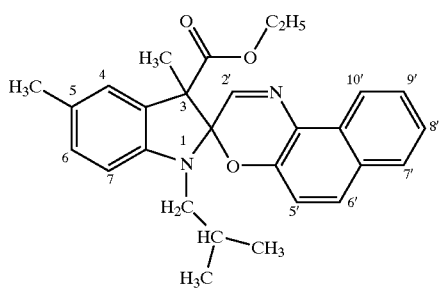

This compound presented a broad absorption band with $\lambda_{max}$ 580, 605 nm in the photoactivated form.

Example 13

1,3-Dimethyl-3-Carboethoxy-8'-(1-Methyl-1-Phenyl)-Ethyl-Spiro-(Indoline-2,3'-(3H)-Naphtho-[2,1-b]-(1,4)-Oxazine)

This compound presented a broad absorption band with $\lambda_{max}$ 577, 599 nm in the photoactivated form.

Example 14

1,3,5,6-Tetramethyl-3-Carboethoxy-Spiro-(Indoline-2,3'-(3H)-Naphtho-[2,1-b]-(1,4)-Oxazine)

This compound presented a broad absorption band with $\lambda_{max}$ 567, 606 nm in the photoactivated form.

Example 15

1-Cyclohexylmethyl-3-Methyl-3-Carboethoxy-6'-Dimethylamino-Spiro-(Indoline-2,3'-(3H)-Naphtho-[2,1-b]-(1,4)-Oxazine)

This compound presented a maximum absorption band with $\lambda_{max}$ 575 nm in the photoactivated form.

Example 16

1-Propyl-3,5-Dimethyl-3-Carboethoxy-Spiro-(Indoline-2,3'-(3H)-Naphtho-[2,1-b]-(1,4)-Oxazine)

This compound presented a maximum absorption band with $\lambda_{max}$ 578, 603 nm in the photoactivated form.

Example 17

1,3-Dimethyl-3-Carboethoxy-6'-Methoxy-Spiro-(Indoline-2,3'-(3H)-Naphtho-[2,1-b]-(1,4)-Oxazine)

This compound presented a maximum absorption band with $\lambda_{max}$ 552 nm in the photoactivated form.

Example 18

1-(2-Phenylethyl)-3-Methyl-3-Carboethoxy-Spiro-(Indoline-2,3'-(3H)-Naphtho-[2,1-b]-(1,4)-Oxazine)

This compound presented a maximum absorption band with $\lambda_{max}$ 600 nm in the photoactivated form.

Example 19

1-Ethyl-3,5-dimethyl-3-Carboethoxy-Spiro-(Indoline-2,3'-(3H)-Naphtho-[2,1-b]-(1,4)-Oxazine)

This compound presented a maximum absorption band with $\lambda_{max}$ 600 nm in the photoactivated form.

Example 20

1-Isobutyl-5-Fluoro-3-Methyl-3-Carboethoxy-Spiro-(Indoline-2,3'-(3H)-Naphtho-[2,1-b]-(1,4)-Oxazine)

This compound presented a maximum absorption band with $\lambda_{max}$ 595 nm in the photoactivated form.

Example 21

For comparison, the spirooxazines described in examples 6–9 above, the new spirooxazine (iii) below and the known spirooxazines depicted by Formulas (i) and (ii) below were individually incorporated (5%) in a polystyrene film of 5 µm.

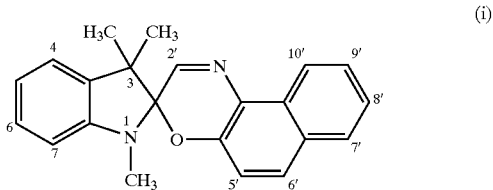

(i)

-continued

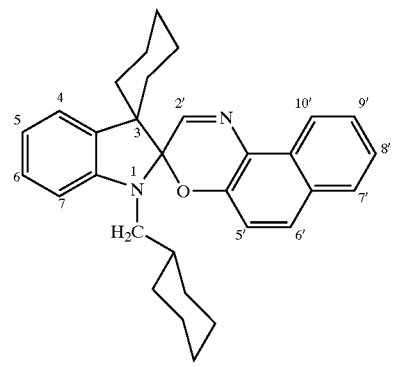
(ii)

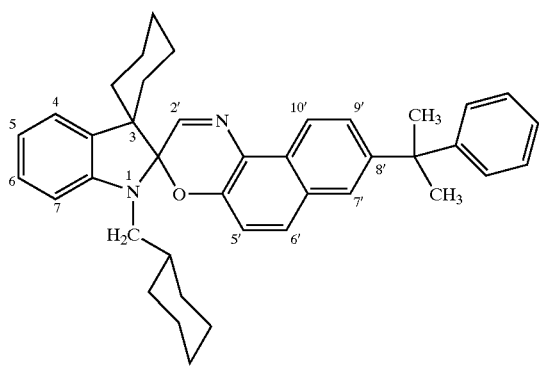
(iii)

The results of the photochromic property examination of the compounds are shown in Table 2, wherein OD is the optical density of the film at the photoinduced color absorption maximum ($\lambda_{max}$), $\tau_{1/2}$ is the halftime of color fading in the dark, and activation time is when the film reaches a steady-state color on irradiation with UV-light of a 250 W mercury lamp. Table 2 shows that substitution of the indoline ring in the 3-position with a carboalkoxy group brings about a profound enhancement in optical density. Examination of the spirooxazine molecular models indicates that this effect may be ascribed to interaction between the carbonyl oxygen and the proton at 2'-position.

Example 22

Preparation of 1-(2,2,2-Trifluoroethyl)-3,3-Dimethyl-6'(4-Diethyl Aminophenyl)-Spiro-(Indoline-2,3'-(3H)-Naphtho[2,1-b]-(1,4)-Oxazine)

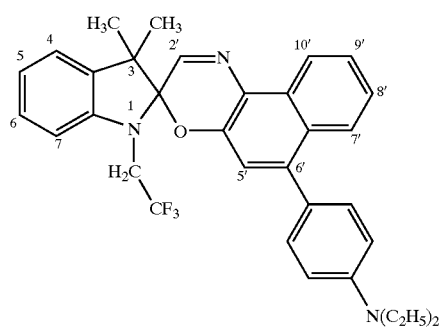
(I'a)

The title compound of formula I'a below was prepared by the following steps:

22a. Preparation of 1-Phenyl-1-(2,2,2-Trifluoroethyl) Hydrazine, Hydrochloric Salt

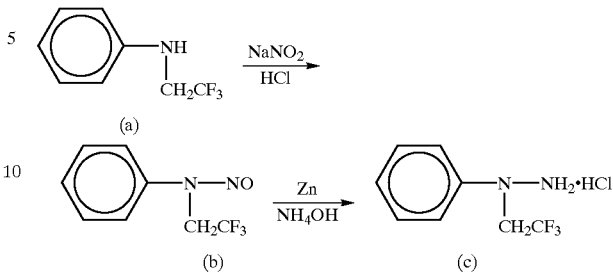

Ten ml of 10% HCl was added to a solution of 2,2,2-trifluoroethyl aniline (1.07 g, 0.0061 mol) in 30 ml dichloromethane. The solution was cooled to 5–7° C. and then a solution of 0.6 g (0.0086 mol) NaNO$_2$ in 2 ml of water was added. After stirring for 2 hours, the lower layer, containing product (b) in CH$_2$Cl$_2$, was separated. The solvent was evaporated and the residue was dissolved in 20 ml of ethanol. 2 g of ammonium carbonate and 4 g Zn powder were added. The mixture was cooled to 5–6° C. and 4.5 ml of 25% NH$_4$OH solution were added very slowly with vigorous stirring. Then 2 g of Zn powder was added again and the mixture was stirred for 10 h.

On completion of the reaction, excess Zn was separated by filtration. The filtrate was diluted with 100 ml of water, and the product was extracted with ethyl ether. After ether evaporation, 10 ml of 10% HCl were added. The precipitated hydrochloric salt of the hydrazine (c) was separated by filtration and washed on filter with ethyl ether (3×10 ml).

22b. Preparation of 1-(2,2,2-Trifluoroethyl)-3,3-Dimethyl-2-Methylene-Indoline

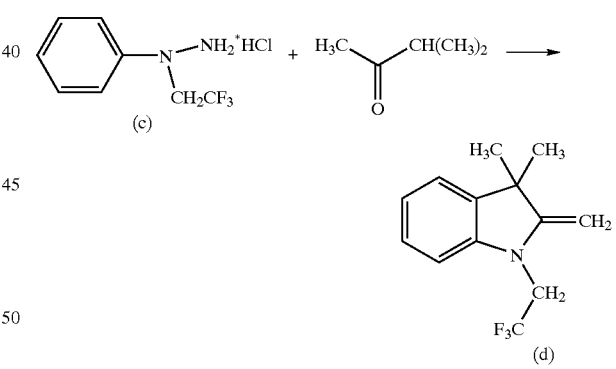

A solution of the hydrochloride (c) obtained above (0.135 g) and methyl isopropyl ketone (0.5 ml) in 10 ml of ethanol was refluxed for 4 hours, followed by addition of 0.3 ml of triethylamine for another hour. After separation of the solvent, the residue was dissolved in 20 ml petroleum ether and stirred for 5 hours with 1 g of activated carbon. Following filtration and evaporation of the solvent, the product (d) was isolated and used further without additional purification.

22c. The final product (I'a) was prepared by reacting the Fisher base (d) and 1-nitroso-2-hydroxy-4-(p-diethylaminophenyl)naphthalene (e), according to procedures well known in the art.

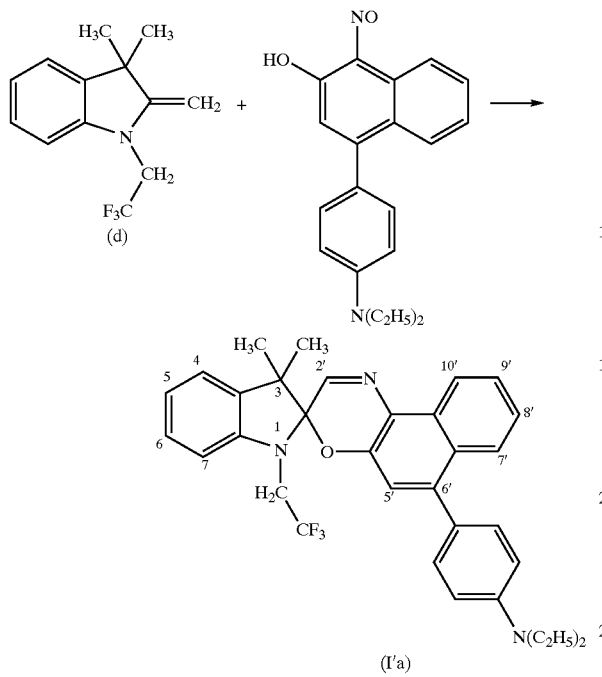

(I'a)

Example 23

For comparison, the photochromic compound 1-neopentyl-3,3-dimethyl-6'-(p-diethylamino-phenyl)-spiro-(indoline-2,3'-(3H)-naphtho-[2,1-b]-(1,4)-oxazine described in Example 10 of U.S. Pat. No. 5,446,151 was synthesized:

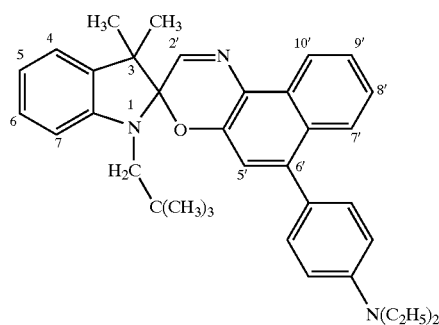

Table 3 gives a comparison of the main characteristics of the photochrome I'a of the invention and the photochrome above described in U.S. Pat. No. 5,446,151, in a polystyrene film.

TABLE 3

| Example | $\lambda_{max}$ | Visual Optical Density in the Photoactivated State | Time of Photoactivation to Steady State, min. | Decoloration Half-time, min |
|---|---|---|---|---|
| 22 | 595 nm | 1.3 | 5 | 10 |
| 23 | 622 nm | 1.25 | 40 | >70 |

The results in Table 3 indicate that compound I'a of the invention has a substantially better photoresponse and a much higher decoloration rate than the compound described in U.S. Pat. No. 5,446,151, which is considered to be a very efficient photochromic dye (D. Clarke et al., Effects in Plastics, SPE, RETTEC, Chicago, 1995).

Example 24

1-(2,2,2-Trifluoroethyl)-3,3-Dimethyl-Spiro-(Indoline-2,3'-(3H)-Naphtho-[2,1-b]-(1,4)-Oxazine), The compound presented an absorbtion band with $\lambda_{max}$ 570 nm in the photoactivated form.

Example 25

1-Cyclohexylmethyl-3,3-Spiro-(Cyclohexyl)-8'-(1-Methyl-1-Phenyl) Ethyl-Spiro-(Indoline-2,3'-(3H)-Naphtho-[2,1-b]-(1,4)-Oxazine), This compound of formula (iii) in Example 21 presented a maximum absorption band with $\lambda_{max}$ 620 nm in the photoactivated form.

Example 26

1-Cyclohexylmethyl-3,3-Dimethyl-8'-(1-Methyl-1-Phenyl)Ethyl-Spiro-(Indoline-2,3'-(3H)-Naphtho-[2,1-b]-(1,4)-Oxazine), This compound presented a broad absorption band with $\lambda_{max}$ 575, 612 nm in the photoactivated form.

Example 27

1-Cyclohexylmethyl-3,3-Dimethyl-6'-Morpholino-8'-(1-Methyl-1-Phenyl)Ethyl-Spiro-(Indoline-2,3'-(3H)-Naphtho-[2,1-b]-(1,4)-Oxazine), The compound presented an absorbtion band with $\lambda_{max}$ 580 nm in the photoactivated form.

Example 28

1-Cyclohexylmethyl-3,3-Dimethyl-6'-Morpholino-8'-(1-Methyl-1-Phenyl)Ethyl-Spiro-(Indoline-2,3'-(3H)-Naphtho-[1,2-b]-(1,4)-Oxazine).

The compound presented an absorbtion band with $\lambda_{max}$ 570 nm in the photoactivated form.

Example 29

1-Propyl-3,5-Dimethyl-3-Carboethoxy-Spiro-(Indoline-2,3'-(3H)-Naphtho-[1,2-b]-(1,4)-Oxazine)

This compound presented a maximum absorption band with $\lambda_{max}$ 603 nm in the photoactivated form.

TABLE 1

| Example No. | $R_1$ | $R_2$ | $R_3$ | $R_4$ | $R_5$ | $\lambda_{max}$ nm | OD at $\lambda_{max}$ | $\tau_{1/2}$ min | Activation time-min |
|---|---|---|---|---|---|---|---|---|---|
| 1 | $CH_3$ | $CH_3$ | $CH_3$ | $OCF_3$ | H | 580 | 0.4 | <0.1 | 3 |
| 2 | $CH_2$-(cyclo)$C_6H_{11}$ | $CH_3$ | $CH_3$ | $OCF_3$ | 6'-$N(CH_3)_2$ | 555 | 2.2 | 5 | 15 |
| 3 | $C_3H_7$ | $CH_3$ | $CH_3$ | $OCF_3$ | 6'-$N(CH_3)_2$ | 550 | 3.0 | 5 | 15 |
| 4 | $C_3H_7$ | $CH_3$ | $CH_3$ | $OCF_3$ | (cyclo)$C_5H_{10}N$ | 558 | 2.5 | 6 | 10 |
| 5 (comp.) | $CH_3$ | $CH_3$ | $CH_3$ | H | H | 598 | 0.3 | 0.5 | 15 |
| 5 (comp.) | $CH_2$-(cyclo)$C_6H_{11}$ | $CH_3$ | $CH_3$ | H | 6'-$N(CH_3)_2$ | 570 | 2.5 | 22 | 30 |

TABLE 2

| Example No. | $R_1$ | $R_2$ | $R_3$ | $R_4$ | $R_5$ | $\lambda_{max}$ nm | OD at $\lambda_{max}$ | $\tau_{1/2}$ min | Activation time-min |
|---|---|---|---|---|---|---|---|---|---|
| 6 | $CH_3$ | $COOC_2H_5$ | $CH_3$ | H | H | 568, 596 | 3.85 | 3.5 | 10 |
| 7 | $CH_2$-(cyclo)$C_6H_{11}$ | $COOC_2H_5$ | $CH_3$ | H | H | 568, 602 | 6.60 | 18 | 40 |
| 8 | $CH_3$ | $COOC_2H_5$ | $CH_3$ | $CH_3, CH_3$ | H | 574, 612 | 3.50 | 7 | 20 |
| 9 | $CH_3$ | $COOC_2H_5$ | $CH_3$ | $CH_3, CH_3$ | $C(CH_3)_2Ph$ | 580, 614 | 3.50 | >20 | 17 |
| 21 (comp.) | $CH_3$ | $CH_3$ | $CH_3$ | H | H | 598 | 0.30 | 0.5 | 1.5 |
| 21 (comp.) | $CH_2$-(cyclo)$C_6H_{11}$ | (cyclo)$C_6H_{11}$ | H | H | | 610 | 0.55 | 0.2 | 10 |
| 21 (comp.) | $CH_2$-(cyclo)$C_6H_{11}$ | (cyclo)$C_6H_{11}$ | H | H | $C(CH_3)_2Ph$ | 620 | 0.70 | 3 | 10 |

What is claimed:

1. A spiro(indoline)naphtho(2,1-b)(1,4)oxazine or spiro(indoline)naphtho(1,2-b)(1,4) oxazine having the following formulas Ia and Ib, respectively:

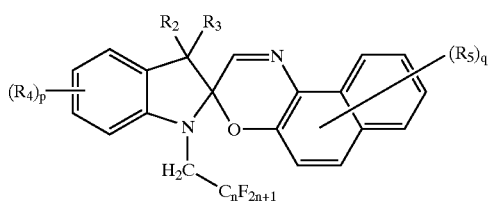

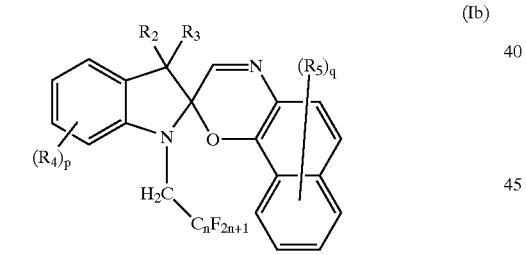

wherein (a) n is an integer from 1 to 6; p is 1 or 2; and q is an integer from 1 to 6;

(b) $R_2$ and $R_3$ represent independently a radical selected from the group consisting of: (i) $C_1$–$C_6$ alkyl optionally substituted by fluoro, $C_1$–$C_4$ alkoxy or fluoroalkoxy, $C_1$–$C_4$ alkylcarbonyloxy, $C_2$–$C_4$ alkenylcarbonyloxy, $C_3$–$C_6$ cycloalkyl or aryl; (ii) $C_2$–$C_6$ alkenyl with a terminal double bond; (iii) $C_3$–$C_6$ cycloalkyl optionally substituted by fluoro; (iv) aryl; (v) alkylcarbonyl; or (vi) one of $R_2$ and $R_3$ is a group —COOR wherein R is a radical (i) to (iv) as defined hereinbefore and the other of $R_2$ and $R_3$ is a radical (i) to (iv) as defined hereinbefore; or (vii) $R_2$ and $R_3$ together with the carbon atom at position 3 of the indoline ring form a 3–7 membered saturated ring optionally containing a heteroatom selected from nitrogen, oxygen or sulfur, and (c) $R_4$ and $R_5$ represent independently (i) hydrogen; (ii) halogen, optionally fluoro; or a radical selected from the group consisting of: (iii) cyano; (iv) aryloxy optionally substituted by $C_1$–$C_6$ alkyl, $C_1$–$C_4$ alkoxy or amino; (v) $C_1$–$C_4$ alkoxy optionally substituted by halogen, preferably di- and trifluoromethoxy; (vii) $C_1$–$C_6$ alkyl optionally substituted by $C_1$–$C_4$ alkoxy, halogen, optionally trifluoromethyl, $C_3$–$C_6$ cycloalkyl, polycycloalkyl (optionally as norbomane or adamantane), aryl or heterocyclyl; (viii) aryl optionally substituted with amino or alkoxy group, optionally dialkylaminophenyl or methoxyphenyl; (ix) amide (—$CONH_2$); (x) sulfonamide (—$SO_2NH_2$); (xi) —$NR_6R_7$, wherein $R_6$ and $R_7$ are independently selected from the group consisting of alkyl, alkenyl, cycloalkyl, aryl, alkylaryl, fluoroalkyl (optionally trifluoromethyl) or $R_6$ and $R_7$ together with the nitrogen atom form a 3–7 membered saturated ring optionally containing a further heteroatom selected from the group consisting of nitrogen, oxygen or sulfur atom, preferably piperidino, piperazino or morpholino; (xii) $R_4$ may further be —$OCF_3$, in which case p is 1; and (xiii) $R_5$ may further be an aryl(dialkyl)methyl group of the formula —$C(aryl)(C_nH_{2n+1})(C_mH_{2m+1})$, wherein n and m are integers from 1 to 5, linked to one of the benzene rings of the naphthoxazine part of the molecule, in which case q is an integer from 1 to 5.

2. A spiro(indoline)naphtho(2,1-b)(1,4)oxazine or spiro(indoline)naphtho(1,2-b)(1,4) oxazine compound containing at the 3-position on the indoline part of the molecule a group —COOR, wherein R is selected from the group consisting of: (i) $C_1$–$C_6$ alkyl optionally substituted by fluoro, $C_1$–$C_4$ alkoxy or fluoroalkoxy, $C_1$–$C_4$ alkylcarbonyloxy, $C_2$–$C_4$ alkenylcarbonyloxy, $C_3$–$C_6$ cycloalkyl or aryl; (ii) $C_1$–$C_6$ alkenyl with a terminal double bond; (iii) $C_3$–$C_6$ cycloalkyl; or (iv) aryl.

3. A spiro(indoline)naphtho(2,1-b)(1,4)oxazine or spiro(indoline)naphtho(1,2-b)(1,4) oxazine according to claim 2, having the formulas IIa and IIb, respectively

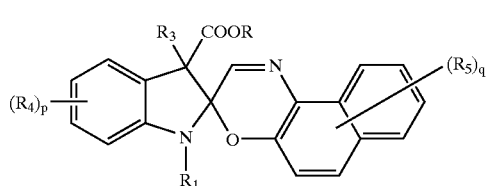

(IIa)

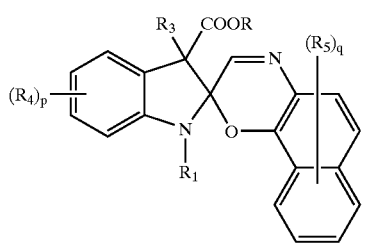

(IIb)

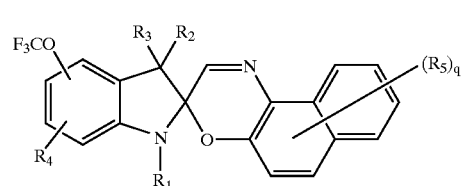

(IIIa)

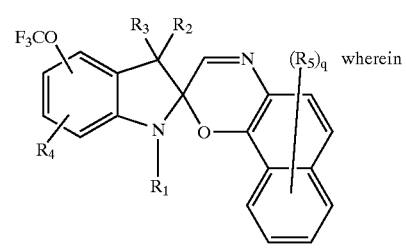

(IIIb)

wherein a. p is 1 or 2 and q is an integer from 1 to 6;
b. $R_1$ is a radical selected from the group consisting of: (i) $C_1$–$C_6$ alkyl optionally substituted by $C_1$–$C_4$ alkoxy, $C_1$–$C_4$ alkylcarbonyloxy, $C_2$–$C_4$ alkenylcarbonyloxy, $C_3$–$C_6$ cycloalkyl, polycycloalkyl, aryl or heterocyclic ring; (ii) $C_3$–$C_6$ cycloalkyl; (iii) polycycloalkyl: (iv) aryl; (v) heterocyclic ring; (vi) —$CH_2$—$C_nF_{2n+1}$ wherein n is an integer of 1 to 6; or (vii) $C_2$–$C_6$ alkenyl with a terminal double bond;
c. $R_3$ represents a radical selected from the group consisting of: (i) $C_1$–$C_6$ alkyl optionally substituted by fluoro, $C_1$–$C_4$ alkoxy or fluoroalkoxy, $C_1$–$C_4$ alkylcarbonyloxy, $C_2$–$C_4$ alkenylcarbonyloxy, $C_3$–$C_6$ cycloalkyl or aryl; (ii) $C_2$–$C_6$ alkenyl with a terminal double bond; (iii) $C_3$–$C_6$ cycloalkyl optionally substituted by fluoro ; and (iv) aryl; and
d. $R_4$ and $R_5$ represent independently (i) hydrogen; (ii) halogen, optionally fluoro; or a radical selected from the group consisting of: (iii) cyano; (iv) aryloxy optionally substituted by $C_1$–$C_6$ alkyl, $C_1$–$C_4$ alkoxy or amino; (v) $C_1$–$C_4$ alkoxy optionally substituted by halogen, preferably di- and trifluoromethoxy; (vii) $C_1$–$C_6$ alkyl optionally substituted by $C_1$–$C_4$ alkoxy, halogen, optionally trifluoromethyl, $C_3$–$C_6$ cycloalkyl, polycycloalkyl (optionally as norbomane or adamantane), or aryl (viii) aryl optionally substituted with amino or alkoxy group, preferably dialkylaminophenyl or methoxyphenyl; (ix) amide (—$CONH_2$); (x) sulfonamide (—$SO_2NH_2$); (xi) —$NR_6R_7$, wherein $R_6$ and $R_7$ are independently selected from the group consisting of alkyl, alkenyl, cycloalkyl, aryl, alkylaryl, fluoroalkyl (optionally trifluoromethyl) or $R_6$ and $R_7$ together with the nitrogen atom form a 3–7 membered saturated ring optionally containing a further heteroatom selected from nitrogen, oxygen or sulfur atom, optionally piperidino, piperazino or morpholino; (xii) $R_4$ may further be —$OCF_3$, in which case p is 1; and (xiii) $R_5$ may further be an aryl(dialkyl)methyl group of the formula —$C(aryl)(C_nH_{2n+1})(C_mH_{2m+1})$, wherein n and m are integers from 1 to 5, linked to one of the benzene rings of the naphthoxazine part of the molecule, in which case q is an integer from 1 to 5.

4. A spiro(indoline)naphtho(2,1-b)(1,4)oxazine or spiro (indoline)naphtho(1,2-b)(1,4) oxazine having the formula IIIa and IIIb, respectively:

a. q is an integer from 1 to 6;
b. $R_1$ is a radical selected from the group consisting of: (i) $C_1$–$C_6$ alkyl optionally substituted by $C_1$–$C_4$ alkoxy, $C_1$–$C_4$ alkylcarbonyloxy, $C_2$–$C_4$ alkenylcarbonyloxy, $C_3$–$C_6$ cycloalkyl polycycloalkyl, aryl or heterocyclic ring; (ii) $C_3$–$C_6$ cycloalkyl; (iii) polycycloalkyl: (iv) aryl; (v) heterocyclic ring; (vi) —$CH_2$—$C_nF_{2n+1}$ wherein n is an integer of 1 to 6; and (vi) $C_2$–$C_6$ alkenyl with a terminal double bond;
c. $R_2$ and $R_3$ represent independently a radical selected from the group consisting of: (i) $C_1$–$C_6$ alkyl optionally substituted by fluoro, $C_1$–$C_4$ alkoxy or fluoroalkoxy, $C_1$–$C_4$ alkylcarbonyloxy, $C_2$–$C_4$ alkenylcarbonyloxy, $C_3$–$C_6$ cycloalkyl or aryl; (ii) $C_2$–$C_6$ alkenyl with a terminal double bond; (iii) $C_3$–$C_6$ cycloalkyl optionally substituted by fluoro; (iv) aryl; or (v) alkylcarbonyl; or (vi) one of $R_2$ and $R_3$ is a group —COOR wherein R is a radical (i) to (iv) as defined hereinbefore and the other of $R_2$ and $R_3$ is a radical (i) to (iv) as defined hereinbefore; or (vii) $R_2$ and $R_3$ together with the carbon atom at position 3 of the indoline ring form a 3–7 membered saturated ring optionally containing a heteroatom selected from nitrogen, oxygen or sulfur, and
d. $R_4$ and $R_5$ represent independently (i) hydrogen; (ii) halogen, optionally fluoro; or a radical selected from the group consisting of: (iii) cyano; (iv) aryloxy optionally substituted by $C_1$–$C_6$ alkyl, $C_1$–$C_4$ alkoxy or amino; (v) $C_1$–$C_4$ alkoxy optionally substituted by halogen, preferably di- and trifluoromethoxy; (vii) $C_1$–$C_6$ alkyl optionally substituted by $C_1$–$C_4$ alkoxy, halogen, optionally trifluoromethyl, $C_3$–$C_6$ cycloalkyl, polycycloalkyl (optionally norbornane or adamantane), or aryl; (viii) aryl optionally substituted with amino or alkoxy group, preferably dialkylaminophenyl or methoxyphenyl; (ix) amide (—$CONH_2$); (x) sulfonamide (—$SO_2NH_2$); (xi) —$NR_6R_7$, wherein $R_6$ and $R_7$ are independently selected from the group consisting of alkyl, alkenyl, cycloalkyl, aryl, alkylaryl, fluoroalkyl (optionally trifluoromethyl) or $R_6$ and $R_7$ together with the nitrogen atom form a 3–7 membered saturated ring optionally containing a further heteroatom selected from nitrogen, oxygen or sulfur atom, optionally piperidino, piperazino or morpholino; and (xii) $R_5$ may further be an aryl(dialkyl)methyl group of the formula —$C(aryl)(C_nH_{2n+1})(C_mH_{2m+1})$, wherein n and m are integers from 1 to 5, linked to one of the benzene rings of the naphthoxazine part of the molecule, in which case q is an integer from 1 to 5.

5. A spiro(indoline)naphtho(2,1-b)(1,4)oxazine or spiro(indoline)naphtho(1,2-b)(1,4) oxazine having the formulas IVa and IVb, respectively:

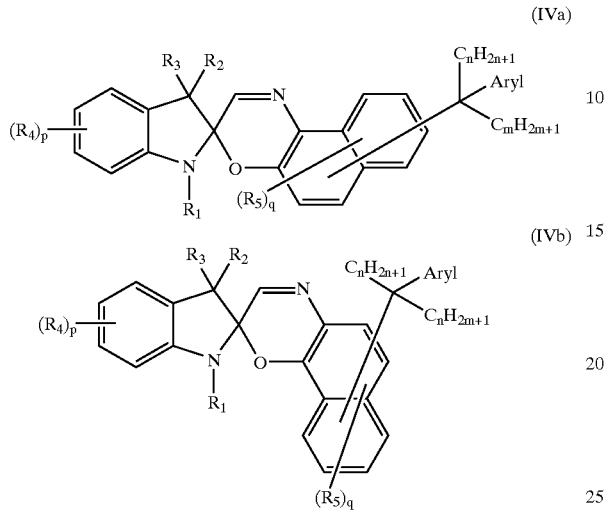

wherein
a. p is 1 or 2 and q is an integer from 1 to 5;
b. $R_1$ is a radical selected from the group consisting of: (i) $C_1$–$C_6$ alkyl optionally substituted by $C_1$–$C_4$ alkoxy, $C_1$–$C_4$ alkylcarbonyloxy, $C_2$–$C_4$ alkenylcarbonyloxy, $C_3$–$C_6$ cycloalkyl, polycycloalkyl, aryl or heterocyclic ring; (ii) $C_3$–$C_6$ cycloalkyl; (iii) polycycloalkyl: (iv) aryl; (v) heterocyclic ring; (vi) —$CH_2$—$C_nF_{2n+1}$ wherein n is an integer of 1 to 6; and (vii) $C_2$–$C_6$ alkenyl with a terminal double bond;
c. $R_2$ and $R_3$ represent independently a radical selected from the group consisting of: (i) $C_1$–$C_6$ alkyl optionally substituted by fluoro, $C_1$–$C_4$ alkoxy or fluoroalkoxy, $C_1$–$C_4$ alkylcarbonyloxy, $C_2$–$C_4$ alkenylcarbonyloxy, $C_3$–$C_6$ cycloalkyl or aryl; (ii) $C_2$–$C_6$ alkenyl with a terminal double bond; (iii) $C_3$–$C_6$ cycloalkyl optionally substituted by fluoro; (iv) aryl; or (v) alkylcarbonyl; or (vi) one of $R_2$ and $R_3$ is a group —COOR wherein R is a radical (i) to (iv) as defined hereinbefore and the other of $R_2$ and $R_3$ is a radical (i) to (iv) as defined hereinbefore; or (vii) $R_2$ and $R_3$ together with the carbon atom at position 3 of the indoline ring form a 3–7 membered saturated ring optionally containing a heteroatom selected from the group consisting of nitrogen, oxygen or sulfur, and
d. $R_4$ and $R_5$ represent independently (i) hydrogen; (ii) halogen, optionally fluoro; or a radical selected from the group consisting of: (iii) cyano; (iv) aryloxy optionally substituted by $C_1$–$C_6$ alkyl, $C_1$–$C_4$ alkoxy or amino; (v) $C_1$–$C_4$ alkoxy optionally substituted by halogen, optionally di- and trifluoromethoxy; (vii) $C_1$–$C_6$ alkyl optionally substituted by $C_1$–$C_4$ alkoxy, halogen, preferably trifluoromethyl, $C_3$–$C_6$ cycloalkyl, polycycloalkyl (optionally norbomane or adamantane), aryl or heterocyclyl; (viii) aryl optionally substituted with amino or alkoxy group, preferably dialkylaminophenyl or methoxyphenyl; (ix) amide (—$CONH_2$); (x) sulfonamide (—$SO_2NH_2$); (xi) —$NR_6R_7$, )wherein $R_6$ and $R_7$ are independently selected from the group consisting of alkyl, alkenyl, cycloalkyl, aryl, alkylaryl, fluoroalkyl (optionally trifluoromethyl) or $R_6$ and $R_7$ together with the nitrogen atom form a 3–7 membered saturated ring optionally containing a further heteroatom selected from nitrogen, oxygen or sulfur atom, optionally piperidino, piperazino or morpholino; and (xii) $R_4$ may further be —$OCF_3$, in which case p is 1.

6. A spiro(indoline)naphtho(2,1-b)(1,4)oxazine or spiro (indoline)naphtho(1,2-b)(1,4) oxazine selected from the compounds consisting of:
1,3,3-trimethyl-5-trifluoromethoxy-spiro-(indoline-2,3'-(3H)-naphtho[2,1-b]-(1,4)-oxazine)
1-Cyclohexylmethyl-3,3-dimethyl-5-trifluoromethoxy-6'-dimethyl-amino-spiro-(indoline-2,3'-(3H)-naphtho[2,1-b]-(1,4)-oxazine)
1-Propyl-3,3-dimethyl-5-trifluoromethoxy-6'-dimethylamino-spiro-(indoline-2,3'-(3H)-naphtho[2,1-b]-(1,4)-oxazine)
1-Propyl-3,3-dimethyl-5-trifluoromethoxy-6'-piperidino-spiro-(indoline-2,3'-(3H)-naphtho-[2,1-b]-(1,4)-oxazine)
1,3-Dimethyl-3-carboethoxy-spiro-(indoline-2,3'-(3H)-naphtho[2,1-b]-(1,4)-oxazine)
1-Cyclohexylmethyl-3-methyl-3-carboethoxy-spiro-(indoline-2,3'-(3H)-naphtho [2,1-b]-(1,4)-oxazine
1,3,4,5-Tetramethyl-3-carboethoxy-spiro-(indoline-2,3'-(3H)-naphtho-[2,1-b ]-(1,4)-oxazine)
1,3,4,5-Tetramethyl-3-carboethoxy-8'-(1-methyl-1-phenyl)ethyl-spiro-(indoline-2,3'-(3H)-naphtho[2,1-b]-(1,4)-oxazine)
1,3-Dimethyl-3-carboethoxy-9'-acetyloxy-spiro-(indoline-2,3'-(3H)-naphtho-[2,1-b]-(1,4)-oxazine)
1-Isobutyl-3-methyl-3-carboethoxy-spiro-(indoline-2,3'-(3H)-naphtho-[2,1-b ]-(1,4)-oxazine)
1-Isobutyl-3,5-dimethyl-3-carboethoxy-spiro-(indoline-2,3'-(3H)-naphtho-[2,1-b]-(1,4)-oxazine)
1,3-Dimethyl-3-carboethoxy-8'-(1-methyl-1-phenyl)-ethyl-spiro-(indoline-2,3'-(3H)-naphtho-[2,1-b]-(1,4)-oxazine)
1,3,5,6-Tetramethyl-3-carboethoxy-spiro-(indoline-2,3'-(3H)-naphtho-[2,1-b ]-(1,4)-oxazine)
1-Cyclohexylmethyl-3-methyl-3-carboethoxy-6'-dimethylamino-spiro-(indoline-2,3'-(3H)-naphtho-[2,1-b]-(1,4)-oxazine)
1-Propyl-3,5-Dimethyl-3-carboethoxy-spiro-(indoline-2,3'-(3H)-naphtho-[2,1-b]-(1,4)-oxazine)
1,3-Dimethyl-3-carboethoxy-6'-methoxy-spiro-(indoline-2,3'-(3H)-naphtho-[2,1-b]-(1,4)-oxazine)
1-(2-Phenylethyl)-3-methyl-3-carboethoxy-spiro-(indoline-2,3'-(3H)-naphtho-[2,1-b]-(1,4)-oxazine)
1-Ethyl-3,5-dimethyl-3-carboethoxy-spiro-(indoline-2,3'-(3H)-naphtho-[2,1-b]-(1,4)-oxazine)
1-Isobutyl-5-fluoro-3-methyl-3-carboethoxy-spiro-(indoline-2,3'-(3H)-naphtho-[2,1-b]-(1,4)-oxazine)
1-(2,2,2-trifluoroethyl)-3,3-dimethyl-6'(4-diethylaminophenyl)-spiro-(indoline-2,3'-(3H)-naphtho-[2,1-b]-(1,4)-oxazine)
1-(2,2,2-Trifluoroethyl)-3,3-dimethyl-spiro-(indoline-2,3'-(3H)-naphtho-[2,1-b]-(1,4)-oxazine)
1-Cyclohexylmethyl-3,3-spiro-(cyclohexyl)-8'-(1-methyl-1-phenyl)ethyl-spiro-(indoline-2,3'-(3H)-naphtho-[2,1-b]-(1,4)-oxazine)
1-Cyclohexylmethyl-3,3-dimethyl-8'-(1-methyl-1-phenyl)ethyl-spiro-(indoline-2,3'-(3H)-naphtho-[2,1-b]-(1,4)-oxazine)

1-Cyclohexylmethyl-3,3-dimethyl-6'-morpholino-8'-(1-methyl-1-phenyl) ethyl-spiro-(indoline-2,3'-(3H)-naphtho-[2,1-b]-(1,4)-oxazine)

1-Cyclohexylmethyl-3,3-dimethyl-6'-morpholino-8'-(1-methyl-1-phenyl) ethyl-spiro-(indoline-2,3'-(3H)-naphtho-[1,2-b]-(1,4)-oxazine)

1-Propyl-3,5-Dimethyl-3-carboethoxy-spiro-(indoline-2,3'-(3H)-naphtho-[1,2-b]-(1,4)-oxazine).

7. A spiro (indoline) naphtha(2,1-b) (1,4) oxazine or a spiro (indoline) naphtha (1, 2-b) (1,4) oxazine compound according to claim 1, further containing at the 3-position on the indoline part of the molecule a group —COOR wherein R is selected from the group consisting of:

a. $C_1$–$C_6$ alkyl optionally substituted by fluoro, $C_{1-C4}$ alkoxy or fluoroalkoxy, $C_1$–$C_4$ alkylcarbonyloxy, $C_2$–$C_4$ alkenylcarbonyloxy, $C_3$–$C_6$ cyclozlkyl or aryl;

b. $C_2$–$C_6$ alkenyl with a terminal double bond;

c. $C_3$–$C_6$ cycloalkyl; or d. Aryl.

* * * * *